United States Patent [19]
Johnson et al.

[11] Patent Number: 5,965,603
[45] Date of Patent: Oct. 12, 1999

[54] NONAQUEOUS COMPOSITIONS FOR PARENTERAL ADMINISTRATION

[75] Inventors: David Farley Johnson, Yardley, Pa.; James M. Quinlan, Mercerville, N.J.

[73] Assignee: American Cyanamid Company, Madison, N.J.

[21] Appl. No.: 09/111,951

[22] Filed: Jul. 8, 1998

Related U.S. Application Data

[60] Provisional application No. 60/053,234, Jul. 21, 1997.
[51] Int. Cl.⁶ .......................... A61K 31/335; A61K 47/00
[52] U.S. Cl. .......................... 514/450; 514/778; 514/975
[58] Field of Search .................................... 514/450, 778, 514/975

[56] References Cited

U.S. PATENT DOCUMENTS 4,978,675  12/1990  Ward et al. .............................. 514/450

FOREIGN PATENT DOCUMENTS

97/11709  4/1997  WIPO ............................ A61K 31/71

OTHER PUBLICATIONS

CA 126:297674, Harvey, Apr. 1997.
CA 108:37508, Glaxo Group Ltd., UK, Oct. 1986.
Lerk, Peter C., et al., Pharmaceutical Development and Technology, 1(1), 27–26 (1996).
Lerk, Peter C., Characterization and Pharmaceutical Application of New Polyoxyethylene–glycol Free Surfactants, in Particular Sucrose Laurate, Ph.D. Thesis submitted to the Faculty of Natural Sciences, University of Basel, Amersfoort, 1991.
Hahn, Lorenz, Bioabbaubare Tenside, Ph.D. Thesis Submitted to the Faculty of Natural Sciences, University of Basel, Basel, 1988.

*Primary Examiner*—Kimberly Jordan
*Attorney, Agent, or Firm*—Timothy J. Babcock

[57] ABSTRACT

The present invention provides nonaqueous compositions comprising a saccharide fatty acid ester and an active compound. The nonaqueous compositions of this invention may be parenterally administered to animals and humans. In particular, the nonaqueous compositions of the present invention are useful for preventing, controlling or treating helminth, acarid or arthropod endo- or ectoparasitic infection or infestation in warm-blooded animals.

22 Claims, No Drawings

NONAQUEOUS COMPOSITIONS FOR PARENTERAL ADMINISTRATION

This application claims the benefit of U.S. Provisional Application No. 60/053,234, filed Jul. 21, 1997.

BACKGROUND OF THE INVENTION

Aqueous compositions containing water-insoluble active compounds and a solubilizing agent have been used for parenteral administration. Solubilizing agents are utilized in those compositions to increase the solubility of the active compound in water. The most widely used solubilizing agents contain polyoxyethylene groups. However, it is generally believed that solubilizing agents which contain those groups may cause adverse reactions which may be anaphylactoid in nature.

To overcome the problems associated with the use of solubilizing agents which contain polyoxyethylene groups, aqueous compositions containing sucrose fatty acid esters have been described. However, aqueous compositions containing sucrose fatty acid esters are not entirely satisfactory because they are not stable for long periods of time. To avoid the storage stability problems associated with the use of aqueous compositions containing sucrose fatty acid esters, waterfree preformulates such as spraydried products and lyophilizates have been described. However, waterfree preformulations are not entirely desirable because reconstitution is time consuming and inconvenient; and the reconstituted product has a short shelf-life.

What is lacking in the art is a composition which: (1) solubilizes a water-insoluble active compound, (2) avoids the problems associated with the use of polyoxyethylene containing solubilizing agents, (3) does not require the use of waterfree preformulations, and (4) is storage stable for prolonged periods of time.

It is therefore an object of the present invention to provide a composition for parenteral administration which overcomes all of the disadvantages associated with the art compositions.

It is also an object of the present invention to provide a method for preventing, controlling or treating helminth, acarid or arthropod endo- or ectoparasitic infection or infestation in warm-blooded animals.

Those and other objects of the present invention will become more apparent from the detailed description thereof set forth below.

SUMMARY OF THE INVENTION

The present invention provides nonaqueous compositions for parenteral administration which comprise about 0.001 to 25t w/v of a substantially water-insoluble active compound, about 0.1 to 70% w/v of a saccharide fatty acid ester, and about 20 to 99% w/v of a pharmaceutically acceptable water-miscible solvent.

The present invention further provides a method for preventing, controlling or treating helminth, aicarid or arthropod endo- or ectoparasitic infection or infestation in warm-blooded animals which method comprises parenterally administering to the warm-blooded animals an anthelmintically, acaricidally or arthropod endo- or ectoparasiticidally effective amount of a nonaclueous composition which comprises about 0.001 to 25% w/v of a substantially water-insoluble macrolide compound, about 0.1 to 70% w/v of a saccharide fatty acid ester, and about 20 to 99% w/v of a pharmaceutically acceptable water-miscible solvent.

Surprisingly, it has been found that the nonaqueous compositions of the present invention avoid all of the problems associated with the aqueous compositions of the art.

DETAILED DESCRIPTION OF THE INVENTION

In accordance with the present invention, the nonaqueous compositions comprise a substantially water-insoluble active compound, a saccharide fatty acid ester, and a pharmaceutically acceptable water-miscible solvent. The invention also provides a method for preventing, controlling or treating helminth, acarid or arthropod endo- or ectoparasitic infection or infestation in warm-blooded animals.

Preferred nonaqueous compositions of this invention comprise about 0.01 to 10% w/v of the active compound, about 1 to 50% w/v of the saccharide fatty acid ester, and about 40 to 99% w/v of the water-miscible solvent. More preferred compositions of the present invention comprise about 0.1 to 5% w/v of the active compound, about 5 to 20% w/v of the saccharide fatty acid ester, and about 70 to 95% w/v of the water-miscible solvent.

The term "saccharide fatty acid ester" as used in the specification and claims refers to the condensation product of a monosaccharide, disaccharide or oligosaccharide or mixture thereof with a $C_4$–$C_{22}$ fatty acid or mixture of $C_4$–$C_{22}$ fatty acids. Monosaccharides which may be used to prepare saccharide fatty acid esters include, but are not limited to, pentoses such as ribose, ribulose, arabinose, xylose, lyxose and xylulose, hexoses such as glucose, fructose, galactose, mannose and sorbose, trioses, tetroses, heptoses, and octoses. Disaccharides which may be used to form the "saccharide" portion of a saccharide fatty acid ester include, but are not limited to, sucrose, maltose, lactose and trehalose.

Fatty acids which may be used to prepare saccharide fatty acid esters include, but are not limited to, $C_4$–$C_{22}$ saturated fatty acids such as caprylic acid, capric acid, lauric acid, myristic acid, palmitic acid and stearic acid, and $C_4$–$C_{22}$ unsaturated fatty acids such as palmitoleic acid, oleic acid, elaidic acid, erucic acid and linoleic acid. Preferred fatty acids include lauric acid, myristic acid and stearic acid. It should be understood that in some instances it is possible for more than one molecule of the fatty acid to react with one molecule of the saccharide to produce saccharide difatty acid esters and in some instances saccharide trifatty acid esters. However, the term saccharide fatty acid ester as used herein preferably refers to saccharide monofatty acid esters. Preferred saccharide fatty acid esters include disaccharide mono$C_8$–$C_{18}$ fatty acid esters such as sucrose monolaurate, sucrose monomyristate and sucrose monostearate.

Pharmaceutically acceptable water-miscible solvents suitable for use in the nonaqueous compositions of this invention include, but are not limited to, alcohols such as ethanol, benzyl alcohol and the like, glycols such as propylene glycol, polyethylene glycols having a molecular weight of less than about 450 and the like, carboxylic acid amides such as N,N-dimethyl acetamide and the like, sulfoxides such as dimethyl sulfoxide and the like, polyhydric alcohols such as glycerol and the like, polyhydric alcohol esters such as triacetin and the like, cyclic ethers such as dimethyl isosorbide and the like, glycerol formal, and 1-methyl-2-pyrrolidinone, and mixtures thereof. Preferred water-miscible solvents include thanol and propylene glycol and mixtures thereof with an ethanol/propylene glycol mixture being more preferred. In a preferred embodiment of the present invention, the active compound is partially soluble, more preferably completely soluble, in the water-miscible solvent.

Advantageously, the present invention overcomes all of the problems associated with the aqueous compositions of the art by using a saccharide fatty acid ester in conjunction with a water-miscible solvent in the absence of water. Uniquely, the nonaqueous compositions of the present invention solubilize a water-insoluble active compound, avoid the use of polyoxyethylene containing solubilizing agents, are ready to use, and are storage stable for prolonged periods of time.

Substantially water-insoluble active compounds useful in the nonaqueous compositions of this invention include, but are not limited to, macrolide compounds such as an LL-F28249α-λ compound, a 23-oxo or 23-imino derivative of an LL-F28249α-λ compound, a milboamycin compound and an avermectin compound, fat-soluble vitamins such as vitamin A, vitamin D, vitamin E and vitamin K, pharmaceutical compounds such as paclitaxel, paclitaxel derivatives, a tetracycline compound, a penicillin compound and a cephalosporin compound, benzoylureas such as flufenoxuron and teflubenzuron, pyriproxyferi, and levamisole, and mixtures thereof. As used herein the term "substantially water-insoluble" means that. the active compound is less than about 10%, preferably less than about 5%, soluble in water.

The macrolide compounds are especially suitable for use in the nonaqueous compositions of this invention. The macrolide compounds include, but are not limited to, those described in U.S. Pat. Nos. 5,019,589; 4,886,828; 5,108,992; 5,030,650 and 5,055,486, incorporated herein by reference.

The preferred macrolide compounds include the compounds designated LL-F28249α-λ which are (collectively) isolates from the fermentation broth of the microorganism *Streptomyces cyaneogriseus* subspecies *noncyanogenus*, deposited in the NRRL under deposit accession No. 15773. The method for preparation of LL-F28249α is disclosed in U.S. Pat. No. 5,106,994 and its continuation, U.S. Pat. No. 5,169,956, incorporated herein by reference.

The LL-F28249α-λ compounds are represented by the following structural formula:

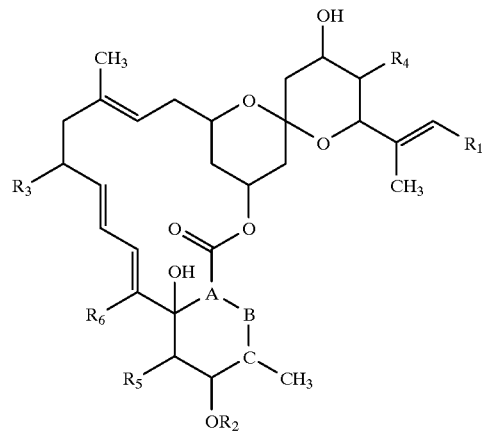

LL-F28249α–γ

| LL-F28249 | $R_1$ | $R_2$ | $R_3$ | $R_4$ | $R_5$ | $R_6$ | $R_5 + R_6$ | A—B | B—C |
|---|---|---|---|---|---|---|---|---|---|
| alpha | $CH(CH_3)_2$ | H | $CH_3$ | $CH_3$ | | | —O—$CH_2$— | CH—CH | CH=C |
| beta | $CH_3$ | H | $CH_3$ | $CH_3$ | | | —O—$CH_2$— | CH—CH | CH=C |
| gamma | $CH_3$ | $CH_3$ | $CH_3$ | $CH_3$ | | | —O—$CH_2$— | CH—CH | CH=C |
| delta | $CH_3$ | $CH_3$ | $CH_3$ | $CH_3$ | OH | $CH_2OH$ | | CH—CH | CH=C |
| epsilon | $CH(CH_3)_2$ | H | H | $CH_3$ | | | —O—$CH_2$— | CH—CH | CH=C |
| zeta | $CH_2CH_3$ | H | $CH_3$ | $CH_3$ | | | —O—$CH_2$— | CH—CH | CH=C |
| eta | $CH(CH_3)_2$ | H | $CH_3$ | $CH_3$ | | | —O—$CH_2$— | C=CH | CH—CH |
| theta | $CH(CH_3)_2$ | H | $CH_3$ | $CH_2CH_3$ | | | —O—$CH_2$— | CH—CH | CH=C |
| iota | $CH(CH_3)_2$ | H | $CH_2CH_3$ | $CH_3$ | | | —O—$CH_2$— | CH—CH | CH=C |
| kappa | $CH_3$ | $CH_3$ | $CH_3$ | $CH_3$ | H | $CH_3$ | | CH—CH | CH=C |
| lambda | $CH(CH_3)_2$ | $CH_3$ | $CH_3$ | $CH_3$ | | | —O—$CH_2$— | CH—CH | CH=C |

The 23-oxo and 23-imino derivatives of LL-F28249α-λ compounds, useful in the nonaqueous compositions of this invention, are disclosed in U.S. Pat. No. 4,916,154, incorporated herein by reference.

A preferred LL-F28249α-λ compound and 23-imino derivative of an LL-F28249α-λ compound useful in the compositions of this invention have the following structural formulas:

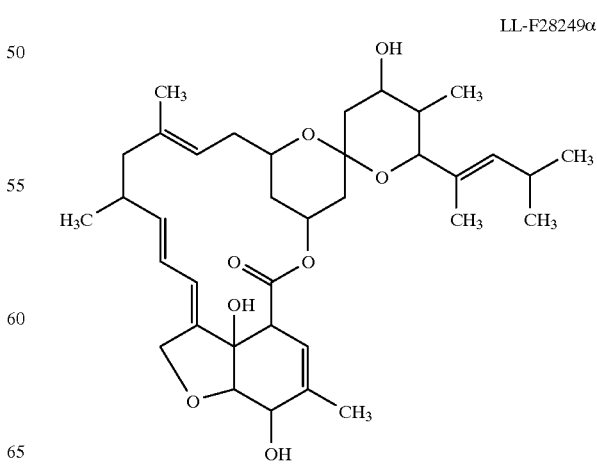

LL-F28249α

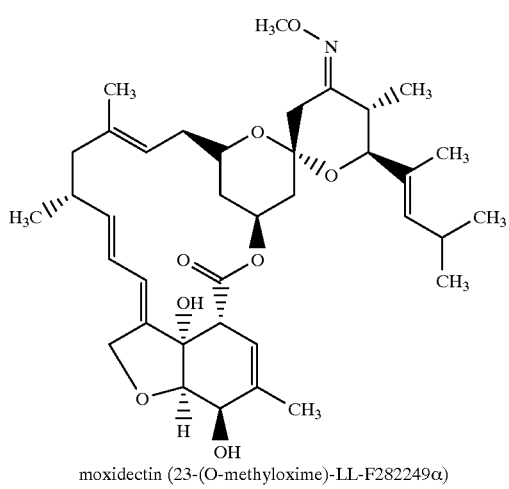

moxidectin (23-(O-methyloxime)-LL-F282249α)

Milbemycin compounds suitable for use in the nonaqueous compositions of this invention include, but 5 are not limited to, milbemycin D, milbemycin oxime and those compounds described in U.S. Pat. Nos. 3,950,360; 4,346,171 and 4,547,520, incorporated herein by reference. Preferred milbemycin compounds for use in this invention are milbemycin D and milbemycin oxime.

Avermectin compounds which are suitable for use in the invention compositions include, but are not: limited to, abamectin, ivermectin, doramectin and those compounds described in U.S. Pat. Nos. 4,199,569 and 4,310,519, incorporated herein by reference, with ivermectin, abamectin and doramectin being preferred. Doramectin and a method for its preparation are described in U.S. Pat. No. 5,089,480, incorporated herein by reference.

A most preferred nonaqueous composition of the present invention which is especially useful when parenterally administered to warm-blooded animals comprises about 0.1 to 2% w/v moxidectin, about 5 to 15% w/v sucrose monolaurate, about 10 to 30% w/v ethanol, and about 60 to 80% w/v propylene glycol.

The nonaqueous compositions of the present invention may be prepared by admixing a mixture of the active compound, saccharide fatty acid ester and water-miscible solvent. In a preferred embodiment of the present invention, the nonaqueous compositions may be prepared by: (1) admixing the active compound with a water-miscible solvent to form a first solution, (2) admixing the saccharide fatty acid ester with propylene glycol to form a second solution, and (3) admixing the first solution with the second solution.

In the compositions of the present invention the saccharide fatty acid ester is preferably present in an amount greater than the active compound. In general, the saccharide fatty acid ester is preferably present in an amount from about 2 times to 30 times, more preferably from about 5 times to 15 times, the amount of the active compound on a weight to volume basis.

When parenterally administered, the nonaqueous compositions of this invention are highly effective for preventing, controlling or treating helminth, acarid and arthropod endo- and ectoparasitic infection and infestation in warm-blooded animals such as cows, sheep, horses, camels, deer, swine, goats, dogs, cats, birds and the like.

Helminthiasis is a widespread disease found in many animals and is responsible for significant economic losses throughout the world. Among the helminths most frequently encountered are the group of worms referred to as nematodes. The nematodes are found in the intestinal tract, heart, lungs, blood vessels and other body tissues of animals and are a primary cause of anemia, weight loss and malnutrition in the infected animals. They do serious damage to the walls and tissue of the organs in which they reside and, if left untreated, may result in death to the infected animals.

The nematodes most commonly found to be the infecting agents of ruminants include Haemonchus and Ostertagia generally found in the abomasum; Cooperia, Trichostrongylus and Nematodirus generally found in the intestinal tract, and Dictyocaulus found in the lungs. In non-ruminant animals important nematodes include Toxocara and Ancylostoma in the intestine and Dirofilaria in the heart of dogs; Ascaridae in the intestine of swine; and large and small strongyles in equines.

Arthropod ectoparasites commonly infecting warm-blooded animals include ticks, mites, lice, fleas, blowfly, the ectoparasite *Lucilia sp.* of sheep, biting insects and migrating dipterous larvae such as *Hypoderma sp.* in cattle, Gastrophilus in horses and *Cuterebra sp.* in rodents.

Treatment of animals to prevent infestation thereof by the above or to reduce or control the proliferation of these infecting agents in animals is thus an important and desirable advantage of the present invention.

In order to facilitate a further understanding of the invention, the following examples are presented primarily for the purpose of illustrating more specific details thereof. The invention is not to be deemed limited thereby except as defined in the claims.

EXAMPLE 1

Preparation of Nonagueous Compositions

A mixture of moxidectin (1.062 kg, 1.05% w/v) and ethanol (20.22 kg, 20.00% w/v) is stirred to obtain a first solution. A mixture of sucrose monolaurate (10.11 kg, 10.00% w/v) and propylene glycol (68.60 kg, 67.85% w/v) is vigorously stirred to obtain a second solution. The first solution is then admixed with the second solution to obtain the nonaqueous composition identified below as composition number 1. The composition weighed 98.90 grams per 100 ml.

| Composition Number 1 | |
|---|---|
| Ingredient | % w/v |
| Moxidectin | 1.05 |
| Sucrose Monolaurate | 10.00 |
| Ethanol | 20.00 |
| Propylene Glycol | 67.85 |

EXAMPLE 2

Evaluation of the Storage Stability of Nonapueous Compositions

The storage stability of the nonaqueous composition prepared in Example 1 is evaluated by storing samples of the composition at 30° C. in an environmental chamber. The samples are removed periodically and visually inspected for physical changes in the appearance of the compositions. The results are summarized in Table I. As can be seen from the data in Table I, the nonaqueous composition of the present invention is storage stable for at least 18 months.

TABLE I

Physical Stability of Nonaqueous Compositions

| Month | Appearance |
|---|---|
| 0 | clear solution |
| 1 | clear solution |
| 2 | clear solution |
| 3 | clear solution |
| 6 | clear solution |
| 12 | clear solution |
| 18 | clear solution |

EXAMPLE 3

Evaluation of Moxidectin Serum Levels in Cattle Treated with a Nonaaueous Composition of the Present Invention Moxidectin serum levels in cattle treated with composition number 1 from Example 1 or a commercial aqueous moxidectin formulation, which comprises a solubilization agent which contains polyoxyethylene groups, are evaluated in this example.

I. Treatments:
A. Moxidectin 1% nonaqueous composition (composition number 1 from Example 1).
B. The commercial moxidectin 1% aqueous injectable solution which contains 20% polysorbate 80 which is a polyoxyethylene containing solubilizing agent.

II. Ration:
The daily ration during the pretreatment and treatment periods consists of 2 kg/animal/day of Pennfield 50900 Textured Stock feed (nominal 16% protein). Grass hay is available ad libitum. Water is available ad libitum from automatic water bowls.

III. Experimental Procedures:
A total of 12 animals are used in this study. On day –7, all animals are weighed. Animals are selected by weight to most closely approximate 150 kg for the smaller animals and 300 kg for the larger animals. Animals are then ranked in decreasing order of weight in blocks of two. A random numbers table is then utilized to assign animals to Treatments A (invention composition) or B (conventional aqueous moxidectin composition). Animals are randomly placed in individual pens for the remainder of the study.

On day 0, the animals are weighed, pretreatment blood is collected and treatment is administered by subcutaneous injection utilizing a syringe. Post-treatment blood is collected at 2, 4, 6, 8, 12, 18, 24, 30 and 36 hours and at 2, 3, 4, 5, 7, 9, 11 and 14 days. Serum is separated, frozen and assayed for moxidectin.

IV. Statistical Analysis:
The maximum concentration ($C_{max}$), the time to maximum concentration ($T_{max}$), the area under the concentration time curve (AUC) and mean residence time (MRT) for Treatments A and B are determined.

V. Results and Discussion:
Individual animal body weights and treatment doses given to each animal are shown in Table II. Animals are dosed with 0.2 mL moxidectin composition/kg body weight to deliver approximately 0.2 mg moxidectin/kg of body weight. All animals are dosed to the next highest 0.2 mL.

Mean serum moxidectin concentrations are determined for each sampling time and are shown in Table III by treatment and by animal size. The results of the statistical analysis are summarized in Table IV. All statistical results are based on the analyses and calculations performed on the estimated mean values. The mean residence time (MRT) of the nonaqueous composition for the large and small animals is 66.41 and 77.47 hours, respectively. The MRT of the aqueous composition is 26.45 and 27.00 hours for the large and small animals, respectively.

The maximum concentration ($C_{max}$) for the nonaqueous composition is 28.21 and 11.54 ppb and for the aqueous composition is 72.07 and 51.69 ppb for the large and small animals, respectively. The time to maximum concentration ($T_{max}$) is 19.13 and 11.56 hours for the nonaqueous and 5.50 and 6.52 hours for the aqueous composition in the large and small animals, respectively. Finally, the areas under the serum concentrations versus time curve (AUC) are 2,083.48 and 875.27 for the nonaqueous and 1,913.28 and 1,356.75 for the aqueous compositions for the large and small animals, respectively.

As can be seen from the data in Tables III and IV, moxidectin from the nonaqueous composition is absorbed into the bloodstream at a slower rate than moxidectin from the aqueous composition. This results in lower peak blood levels of moxidectin and would provide an increased margin of safety in susceptible animals such ELS young, undernourished cattle. It can also be seen from the data in Table IV that the mean residence time of mcxidectin in cattle treated with the nonaqueous composition is significantly greater than the mean residence time observed with the standard aqueous composition. Accordingly, the nonaqueous composition of the present invention provides a significant improvement over the standard aqueous composition because the safety of moxidectin towards susceptible animals is improved, therapeutic levels of moxidectin are maintained for longer periods of time in large cattle, and the use of a polyoxyethylene containing solubilizing agent is avoided.

TABLE II

Individual Body Weights and Treatment Doses

| Treatment[1] Group | Animal No. | Weight (kg) | Dose (mL) |
|---|---|---|---|
| A | 1 | 151.0 | 3.2 |
|  | 5 | 166.5 | 3.4 |
|  | 6 | 180.0 | 3.6 |
|  | 7 | 310.0 | 6.2 |
|  | 8 | 321.0 | 6.6 |
|  | 9 | 305.5 | 6.2 |
| B | 2 | 150.0 | 3.0 |
|  | 3 | 176.0 | 3.6 |
|  | 4 | 163.5 | 3.4 |
|  | 10 | 319.0 | 6.4 |
|  | 11 | 311.0 | 6.4 |
|  | 12 | 273.0 | 5.6 |

[1]Group A - Moxidectin 1% nonaqueous composition.
Group B - Moxidectin 1% aqueous composition.

TABLE III

Mean Moxidectin Concentrations (ppb)

| Treatment Group[1] | Time | Large Animal Mean | Small Animal Mean |
|---|---|---|---|
| A[2] | Hour 0 | 0.00 | 0.00 |
|  | Hour 2 | 0.00 | 4.10 |
|  | Hour 4 | 14.35 | 6.02 |

TABLE III-continued

Mean Moxidectin Concentrations (ppb)

| Treatment Group[1] | Time | Large Animal Mean | Small Animal Mean |
|---|---|---|---|
| | Hour 6 | 20.78 | 9.71 |
| | Hour 8 | 20.90 | 9.08 |
| | Hour 12 | 26.74 | 12.10 |
| | Hour 18 | 24.39 | 8.98 |
| | Hour 24 | 33.95 | 11.12 |
| | Hour 30 | 25.79 | 8.88 |
| | Hour 36 | 16.14 | 9.67 |
| | Day 2 | 20.60 | 8.63 |
| | Day 3 | 10.97 | 6.39 |
| | Day 4 | 11.11 | — |
| | Day 5 | 5.74 | — |
| B | Hour 0 | 0.00 | 0.00 |
| | Hour 2 | 23.90 | 34.32 |
| | Hour 4 | 88.73 | 34.43 |
| | Hour 6 | 69.24 | 44.17 |
| | Hour 8 | 55.29 | 49.73 |
| | Hour 12 | 49.07 | 37.09 |
| | Hour 18 | 39.28 | 21.67 |
| | Hour 24 | 30.18 | 22.44 |
| | Hour 30 | 27.07 | 19.09 |
| | Hour 36 | 15.37 | 13.55 |
| | Day 2 | 19.24 | 10.37 |
| | Day 3 | 9.47 | 6.73 |
| | Day 4 | 4.88 | — |
| | Day 5 | 7.98 | — |

[1]Treatment Group A animals receive the nonaqueous moxidectin composition and Treatment Group B animals receive the aqueous moxidectin composition.
[2]Animal number 1 in Treatment Group A, small animals, had a positive slope so this animal was eliminated before further calculations were performed.

TABLE IV

Summary of Pharmacokinetic Parameters

| | Treatment Group[1] | |
|---|---|---|
| | A | B |
| Mean Residence Time (hours) | | |
| Large | 66.41 | 26.45 |
| Small | 77.47 | 27.00 |
| $C_{max}$ (ppb) | | |
| Large | 28.21 | 72.07 |
| Small | 11.54 | 51.69 |
| $T_{max}$ (hours) | | |
| Large | 19.13 | 5.50 |
| Small | 11.56 | 6.52 |
| AUC | | |
| Large | 2,083.48 | 1,913.28 |
| Small | 875.27 | 1,356.75 |

[1]Treatment Group A animals receive the nonaqueous moxidectin composition and Treatment Group B animals receive the aqueous moxidectin composition.

What is claimed is:

1. A nonaqueous composition for parenteral administration which comprises about 0.001 to 25% w/v of a substantially water-insoluble active compound, about 0.1 to 70% w/v of a saccharide fatty acid ester, and about 20 to 99% w/v of a pharmaceutically acceptable water-miscible solvent.

2. The composition according to claim 1 wherein the saccharide fatty acid ester is selected from the group consisting of a monosaccharide $C_4$–$C_{22}$ fatty acid ester, a disaccharide $C_4$–$C_{22}$ fatty acid ester and an oligosaccharide $C_4$–$C_{22}$ fatty acid ester and mixtures thereof.

3. The composition according to claim 2 wherein the saccharide fatty acid ester is a disaccharide monoC$_8$–C$_{18}$ fatty acid ester.

4. The composition according to claim 3 wherein the disaccharide monoC$_8$–C$_{18}$ fatty acid ester is a sucrose monoC$_8$–C$_{18}$ fatty acid ester.

5. The composition according to claim 4 wherein the sucrose monoC$_8$–C$_{18}$ fatty acid ester is selected from the group consisting of sucrose monolaurate, sucrose monomyristate and sucrose monostearate and mixtures thereof.

6. The composition according to claim 1 wherein the water-miscible solvent is selected from the group consisting of ethanol, propylene glycol, a polyethylene glycol, benzyl alcohol, N,N-dimethyl acetamide, dimethyl isosorbide, dimethyl sulfoxide, glycerol, triacetin, glycerol formal and 1-methyl-2-pyrrolidinone and mixtures thereof.

7. The composition according to claim 6 wherein the water-miscible solvent is selected from the group consisting of ethanol and propylene glycol and mixtures thereof.

8. The composition according to claim 7 wherein the water-miscible solvent is an ethanol/propylene glycol mixture.

9. The composition according to claim 1 wherein the substantially water-insoluble active compound is selected from the group consisting of a macrolide compound, a fat soluble vitamin, a pharmaceutical compound, a benzoylurea, pyriproxyfen and levamisole and mixtures thereof.

10. The composition according to claim 9 wherein the substantially water-insoluble active compound is selected from the group consisting of an LL-F28249α-λ, a 23-oxo or 23-imino derivative of an LL-F28249α-λ, a milbemycin, an avermectin, vitamin A, vitamin D, vitamin E, vitamin K, paclitaxel, flufenoxuron, teflubenzuron, pyriproxyfen and levamisole and mixtures thereof.

11. The composition according to claim 10 wherein the substantially water-insoluble active compound is moxidectin.

12. The composition according to claim 1 which comprises about 0.01 to 10% w/v of the active compound, about 1 to 50% w/v of the saccharide fatty acid ester, and about 40 to 99% w/v of the water-miscible solvent.

13. The composition according to claim 12 which comprises about 0.1 to 5% w/v of the active compound, about 5 to 20% w/v of the saccharide fatty acid ester, and about 70 to 95% w/v of the water-miscible solvent.

14. The composition according to claim 13 which comprises about 0.1 to 2% w/v moxidectin, about 5 to 15% w/v sucrose monolaurate, about 10 to 30% w/v ethanol, and about 60 to 80% w/v propylene glycol.

15. A method for preventing, or treating helminth, acarid or arthropod endo- or ectoparasitic infection or infestation in a warm-blooded animal which comprises parenterally administering to the animal an anthelmintically, acaricidally or arthropod endo- or ectoparasiticidally effective amount of a nonaqueous composition comprising about 0.001 to 25% w/v of a substantially water-insoluble macrolide compound, about 0.1% to 70% w/v of a saccharide fatty acid ester, and about 20 to 99% w/v of a pharmaceutically acceptable water-miscible solvent.

16. The method according to claim 15 wherein the animal is selected from the group consisting of a cow, a sheep, a horse, a camel, a deer, a swine, a goat, a dog, a cat and a bird.

17. The method according to claim 15 wherein the saccharide fatty acid ester is a disaccharide monoC$_8$–C$_{18}$ fatty acid ester, and the water-miscible solvent is selected from the group consisting of ethanol, propylene glycol, a polyethylene glycol, benzyl alcohol, N,N-dimethyl acetamide, dimethyl isosorbide, dimethyl sulfoxide, glycerol, triacetin, glycerol formal and 1-methyl-2-pyrolidinone and mixtures thereof.

18. The method according to claim 17 wherein the disaccharide mono$C_8$–$C_{18}$ fatty acid ester is selected from the group consisting of sucrose monolaurate, sucrose monomyristate and sucrose monostearate and mixtures thereof, and the water-miscible solvent is selected from the group consisting of ethanol and propylene glycol and mixtures thereof.

19. The method according to claim 15 wherein the macrolide compound is selected from the group consisting of an LL-F28249α-λ, a 23-oxo or 23-imino derivative of an LL-F28249α-λ, a milbemycin and an avermectin and mixtures thereof.

20. The method according to claim 19 wherein the macrolide compound is moxidectin.

21. The method according to claim 15 wherein the composition comprises about 0.1 to 5% w/v of the active compound, about 5 to 20% w/v of the saccharide fatty acid ester, and about 70 to 95% w/v of the water-miscible solvent.

22. The method according to claim 21 wherein the composition comprises about 0.1 to 2% w/v moxidectin, about 5 to 15% w/v sucrose monolaurate, about 10 to 30% w/v ethanol, and about 60 to 80% w/v propylene glycol.

* * * * *